US012670707B2

(12) United States Patent      (10) Patent No.: US 12,670,707 B2

Hong et al.      (45) Date of Patent: Jun. 30, 2026

(54) MACHINE LEARNING ENABLED SYSTEM FOR SKIN ABNORMALITY INTERVENTIONS

(71) Applicant: SKINOPATHY INC., Toronto (CA)

(72) Inventors: Colin Hong, Toronto (CA); Rakesh Joshi, Toronto (CA)

(73) Assignee: SKINOPATHY INC., Toronto (CA)

( * ) Notice: Subject to any disclaimer, the term of this patent is extended or adjusted under 35 U.S.C. 154(b) by 296 days.

(21) Appl. No.: 18/274,918

(22) PCT Filed: Feb. 1, 2022

(86) PCT No.: PCT/CA2022/050145

§ 371 (c)(1),
(2) Date: Jul. 28, 2023

(87) PCT Pub. No.: WO2022/160070

PCT Pub. Date: Aug. 4, 2022

(65) Prior Publication Data

US 2024/0087115 A1     Mar. 14, 2024

Related U.S. Application Data

(60) Provisional application No. 63/144,142, filed on Feb. 1, 2021.

(51) Int. Cl.
   *G06T 7/00*       (2017.01)
   *G06T 7/50*       (2017.01)
   (Continued)

(52) U.S. Cl.
   CPC .............. *G06T 7/0012* (2013.01); *G06T 7/50* (2017.01); *G06T 11/60* (2013.01); *G06V 10/82* (2022.01);
   (Continued)

(58) Field of Classification Search
   CPC ......... G06T 7/0012; G06T 7/50; G06T 11/60; G06T 2207/20084; G06T 2207/30088;
   (Continued)

(56) References Cited

U.S. PATENT DOCUMENTS

| | | | |
|---|---|---|---|
| 2013/0096392 A1* | 4/2013 | Adams ................. | A61B 5/0075 |
| | | | 600/301 |
| 2021/0104043 A1* | 4/2021 | Crawford .............. | G06T 7/0014 |
| 2022/0156932 A1* | 5/2022 | Fujisawa ................ | G16H 30/40 |

FOREIGN PATENT DOCUMENTS

WO     2019230724 A1    12/2019

OTHER PUBLICATIONS

Pham, Tri-Cong, et al. "Deep CNN and data augmentation for skin lesion classification." Asian Conference on Intelligent Information and Database Systems. Cham: Springer International Publishing, 2018.https://link.springer.com/chapter/10.1007/978-3-319-75420-8_54 (Year: 2018).*

(Continued)

*Primary Examiner* — Han Hoang

(74) *Attorney, Agent, or Firm* — Hartman Global IP Law; Gary M. Hartman; Domenica N.S. Hartman

(57) ABSTRACT

Systems and methods for use in classifying and measuring images of skin abnormalities. The systems and methods can be used in an AR enabled system that may be used to assist in skin surgeries and skin abnormality triaging and diagnosis. The system uses a convolutional neural network to classify a skin abnormality in an initial image. The CNN may also be used in determining the boundaries of the skin abnormality. A fiducial marker may be present in the initial image and this marker may be used in automatically measuring the size of the skin abnormality. An adjusted image is generated based on the measured abnormality and this (Continued)

adjusted image can be used as an overlay in an AR enabled system for use in assisting surgical procedures.

13 Claims, 15 Drawing Sheets

(51) Int. Cl.
| | |
|---|---|
| *G06T 11/60* | (2006.01) |
| *G06V 10/82* | (2022.01) |
| *G16H 30/40* | (2018.01) |

(52) U.S. Cl.
CPC ... *G16H 30/40* (2018.01); *G06T 2207/20084* (2013.01); *G06T 2207/30088* (2013.01); *G06T 2207/30096* (2013.01); *G06T 2207/30204* (2013.01)

(58) Field of Classification Search
CPC ........... G06T 2207/30096; G06T 2207/30204; G06V 10/82; G06V 40/10; G16H 30/40; G16H 40/63; G16H 20/40; G16H 50/20; G16H 50/70; A61B 5/441; A61B 5/7267; A61B 5/00; G06N 3/045; G06N 3/08
See application file for complete search history.

(56) References Cited

OTHER PUBLICATIONS

Saini, Shreshth, Divij Gupta, and Anil Kumar Tiwari. "Detector-segmentor network for skin lesion localization and segmentation." National Conference on Computer Vision, Pattern Recognition, Image Processing, and Graphics. Singapore: Springer Singapore, 2019. (Year: 2019).*

[Continuation of Item V] https://link.springer.com/chapter/10.1007/978-981-15-8697-2_55 (Year: 2019).*

Monkman, GG, et. al., "Using Machine Vision to Estimate Fish Length from Images Using Regional Convolutional Neural Networks", Citation for published version: Monkman, GG, Hyder, K, Kaiser, MJ & Vidal, FP 2019, 'Using 1 machine vision to estimate fish length from images using regional convolutional neural networks', Methods in Ecology and Evolution, vol. 10, No. 12, pp. 2045-2056. https://doi.org/10.1111/2041-210X.13282.

Öztürk, S. et. al., "Skin Lesion Segmentation with Improved Convolutional Neural Network", Springer, Journal of Digital 2 Imaging (2020) 33: pp. 958-970.

International Search Report and Written Opinion for International Application No. PCT/CA2022/050145, dated Mar. 8, 2022, (10 pages).

* cited by examiner

130

300

310    CNN BASE MODEL    320    330

STEM MODULE     BUILDING MODULES     FINAL MODULE     DENSE LAYERS

CNN:CNN-based Boundary Attention Mapper

|  | precision | recall | f1-score | support |
|---|---|---|---|---|
| bcc | 0.91 | 0.82 | 0.86 | 73 |
| oth_lm | 0.79 | 0.94 | 0.86 | 16 |
| scc | 0.82 | 0.88 | 0.85 | 51 |
| accuracy |  |  | 0.86 | 140 |
| macro avg | 0.84 | 0.88 | 0.86 | 140 |
| weighted avg | 0.86 | 0.86 | 0.86 | 140 |

MACHINE LEARNING ENABLED SYSTEM FOR SKIN ABNORMALITY INTERVENTIONS

TECHNICAL FIELD

The present invention relates to the field of machine learning as applied to image analysis. More specifically, the present invention relates to systems and methods that incorporate machine learning while providing tools for use by medical personnel.

BACKGROUND

The human integumentary system, including the skin, can become abnormal due to internal and external agents of change, from cancer to thermal burns [1]. Machine learning techniques, specifically the use of convolutional neural networks (CNN) or convnets, have been used to classify and segment skin cancer lesions from dermatoscopic, clinical and camera medical images [2,3,4,5]. In a CNN, images are treated as tensors and are passed through an architecture, made up of layers of artificial neurons, some performing convolutional operations and others performing pooling functions [6,7]. These layers are interspersed with activation functions through which the tensor information is passed as a set of weights. The entire construct acts as a computational graph. First, a set of images is used to train the construct, and subsequently, another set of images is used to validate the accuracy of the classifier. This is done with weights moving in both directions, referred to as forward pass and back-propagation, continuously undergoing loss minimization between the true class or the "ground-truth" of an image and the CNN-predicted class of an image. The construct of the CNN, if having a linear architecture, also allows for the extraction of feature maps, on what features of the image the model is "seeing" in terms of contours, but also the features of the image that the model uses to make a decision when classifying an image.

As noted above, there have been previous attempts at using CNN-based technology to classify images of skin abnormalities. However, such attempts do not have success rates that are acceptable.

There is therefore a need for technologies that provide better success rates and can be used for other ends.

SUMMARY

The present invention provides systems and methods for use in classifying, measuring images of skin abnormalities. The systems and methods can be used in an AR enabled system that may be used to assist in skin surgeries and skin abnormality triaging and diagnosis. The system uses a convolutional neural network to classify a skin abnormality in an initial image. The CNN may also be used in determining the boundaries of the skin abnormality. A fiducial marker may be present in the initial image and this marker may be used in automatically measuring the size of the skin abnormality. An adjusted image is generated based on the measured abnormality and this adjusted image can be used as an overlay in an AR enabled system for use in assisting surgical procedures.

In a first aspect, the present invention provides a system for use with digital images, the system comprising:

a processor for receiving an initial digital image, the initial digital image showing a skin abnormality on a skin of a patient, said processor also being for receiving an adjusted image version of said initial image;

a data communication path for transferring the initial digital image to at least one processing unit, said at least one processing unit comprising at least one convolutional neural network, said at least one processing unit being for classifying and amending said initial digital image to result in an adjusted image, said adjusted image being received by said system after said adjusted image is produced;

a digital imaging device for producing a working image of skin abnormality;

an overlay module for overlaying said adjusted image over said working image such that a skin abnormality in said adjusted image is overlaid over said skin abnormality in said working image.

In a second aspect, the present invention provides a method for processing an initial digital image, the method comprising:

by way of a data processor, receiving said initial digital image, said initial digital image being an image of a skin abnormality on a patient;

using a data communication path, sending said initial digital image to at least one processing unit, said at least one processing unit comprising at least one convolutional neural network (CNN);

using said CNN in said at least one processing unit, classifying at least one element in said initial digital image;

generating an adjusted image from said initial digital image based on a processing of said initial digital image by said at least one processing unit;

by way of said data processor, receiving said adjusted image from said at least one processing unit;

using an overlay module, overlaying said adjusted image over a working image of said skin abnormality.

In a third aspect, the present invention provides computer readable media having encoded thereon computer readable and computer executable code that, when executed, implements a convolutional neural network (CNN) for use in digital image classification, the CNN comprising:

a stem block;

a building module;

a final module;

a dense layer;

wherein outputs of said stem block are received by said building module;

outputs of said building module are received by said final module;

outputs of said final module are received by said dense layer;

variable skipped connections are used by at least one of said stem block and said building module;

said dense layer is a fully connected layer;

attention pixels in an initial image are captured by said final module;

said initial digital image that is to be classified by said CNN is an image of a skin abnormality.

BRIEF DESCRIPTION OF THE DRAWINGS

The embodiments of the present invention will now be described by reference to the following figures, in which identical reference numerals in different figures indicate identical elements and in which.

DETAILED DESCRIPTION

Figure 1:
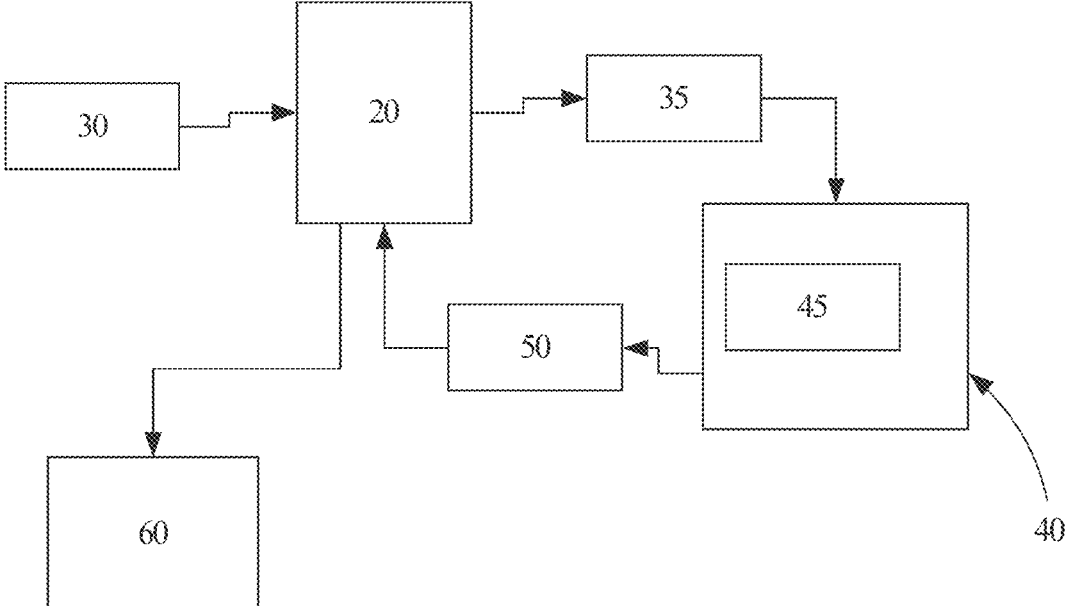
FIG. 1 is a block diagram illustrating the flow between different components in a system according to one aspect of the present invention.

To better understand the present invention, the reader is directed to the listing of citations at the end of this description. For ease of reference, these citations and references have been referred to by their listing number throughout this document. The contents of the citations in the list at the end of this description are hereby incorporated by reference herein in their entirety.

As noted above, CNNs have been used in the past to classify images of skin abnormalities. Numerous open-source CNNs have been modified to tackle the challenges of skin-related classification tasks, primarily for screening for skin cancer or skin disease lesions [2,4]. These CNNs have architectures [2,4,5] and pre-trained weights [6,7] generated from vast datasets [2,4,6] that make them accurate for generalized image classification. However, there are no CNNs designed from scratch, optimized and trained specifically for skin image classification that include both mobile-device camera images as well as dermatoscopic skin images [4]. Current available CNNs are of low value if one wants to use an image of a skin lesion taken from a patient's or physician's mobile device. First, large skin datasets available for training these CNNs are dermatoscopic, and therefore the prediction accuracy achieved on mobile-device camera-based images by transfer learning is low. This is primarily because dermatoscopic images of the skin have a 5x-15x resolution of the skin abnormality [4]. Secondly, there is a higher variance in the quality of images, with respect to resolution, framing of the abnormality, lighting etc., that come from camera-images, while the curated datasets available to train CNNs are highly quality controlled for these parameters[4]. Additionally, these CNNs are pretrained on random images for learning edges and other contours. These make them excellent classifiers for these objects and for extracting high-level features for transfer learning. However, the skin and its abnormalities, especially skin lesions, have fine-grained features that are not present elsewhere and therefore cannot be learned using these strategies, for example the texture and color of normal skin versus that of a skin lesion.

In addition to the above, there are no skin-specific CNNs that use skin-specific, abnormality boundary mapping or contour mapping. There are no machine learning systems that integrate these contour maps with the classifier's attention mapping (also referred to as saliency feature mapping) to understand the classification process of skin abnormalities and to use this valuable information to directly guide a medical intervention [8,9,10]. The current saliency mapping systems only extract decision-making/attention pixels from the latter activation layers of the CNN, either using back-propagation methods or class activation maps.

Understanding the operation of a convnet requires qualitative analysis of learned visualizations and feature activity in the intermediate and higher layers, especially the activation layers associated with the last convolutional layer. Various versions of saliency models are available to detect and segment the object or region of interest [9,10] and put into understanding on how deep CNNs model a class. These works have focused on highlighting significant "attention" pixels using partial derivatives of predicted class scores with respect to pixel intensities (called gradients) or making modifications to raw gradients that excite individual feature maps at any layer in the model [11,12]. Building class specific saliency maps by performing gradient ascent in pixel space is a more recent visualization technique with remarkable localization abilities. CAM and gradient-based CAM, called GradCAM, highlight important regions of the image which correspond to any decision of interest [13]. While both these techniques have been used widely, they underperform when localizing multiple occurrences of the same class and do not capture the entire object in completeness [14]. They are abstract in nature and they do not provide optimal contour or "boundary" mapping of a skin abnormality like a skin lesion. An enhanced visualisation of contour/boundary and salient/"attention" pixels is required to highlight fine-grained features of skin lesion.

Additionally, a computer-vision based system that uses these boundary-attention maps to measure the spatial dimensions of the lesions, in 2-dimensions (area) and in 3-dimensions (relative height/depth) is also preferred. A mobile application that automatically measures the size of skin abnormalities and that displays the final output as an augmented reality object on mobile device screens would aid in medical interventions, including lesion topical treatments and surgery.

The present disclosure is directed to an implementation of a convolutional neural network (CNN), with a novel CNN architecture. In one aspect, there is provided an image processing system for analyzing an object on animal skin, comprising the novel CNN. The CNN uses common CNN building blocks, but in unique permutations that is optimized to take advantage of being trained on proprietary mobile and/or dermatoscopic images that have been pre-processed using a proprietary protocol.

In one or more implementations, the CNN architecture is scaled using common hyperparameter optimization techniques, including neural architecture search using re-enforcement learning, for the number of building blocks (depth) and neurons (width), primarily based on size of the dataset. This allows the CNN to classify datasets of varying sizes by adjusting the architecture. In one or more implementations, the invention further uses an algorithm to find the value of Taylor series approximator for activation functions (permutations of ReLU, Leaky ReLu, Switch and sigmoid functions). This allows for accurate, data-size-guided, approximations of the underlying function(s) in a dataset.

In one or more implementations, the CNN architecture is scaled using the biologically inspired golden ratio for the number of building blocks (depth) and neurons (width), primarily based on size of the classifier. This allows the CNN to classify datasets of varying sizes by adjusting the architecture. In one or more implementations, the invention further uses an algorithm to find the value of Taylor series approximator for activation functions (permutations of ReLU and sigmoid functions) based off the square root of the golden ratio. This allows for accurate, data-size-guided, approximations of the underlying function(s) in a dataset. To make the weight initialization non-arbitrary, in an activation-function juncture, a novel golden-ratio based weight initialization operation is used.

In one or more implementations, the CNN of the present disclosure is pre-processed for CNN classification using a texture optimization, inspired by grey level co-occurrence matrix (GLCM), termed Skin-specific 2nd-order grey level co-occurrence matrix (sGLCM), that makes the image recognition process sensitive to "abnormal" versus "normal" skin, where "abnormal" includes, but is not exclusively defined by skin cancer lesions, other non-cancerous dermatological conditions, etc. It should be clear that the various aspects of the present invention may be used in relation to skin abnormalities that include cancerous skin lesions that may need to be surgically removed, melanomas, basal cell carcinomas, squamous cell carcinomas, and dysplastic nevus.

In one or more implementations, the images to train the CNN of the present disclosure is pre-processed for segmentation of "abnormal" versus "normal" skin, where "abnormal" includes, but is not exclusively defined by, skin lesions. This is done by the use of a separate, pre-trained CNN that creates masked images that are used for the training of the classifier CNN.

In one or more implementations, the classifier CNN of the present disclosure is trained, using two strategies that takes advantage of open-source generic datasets, for example ImageNet [6], open-source skin lesion datasets, for high-level feature extraction, but relies primarily on skin datasets of dermatoscopic and mobile-device camera images.

In one or more implementations, the CNN of the present disclosure is used to produce composite skin saliency feature maps using an innovative Boundary-Attention Mapper (BAM) system to understand the pixel-based contours that the algorithm visualizes in the early activation layers as well as the decision-making pixels of the CNN penultimate layers. The result is a CNN-based Boundary Attention Mapper component.

In one or more implementations, the Boundary-Attention Mapper (BAM) integrates 1) a method of a highly contour-discriminative localization of skin lesions by utilizing activation layers, and permutations thereof, from the stem module of the described CNN to create fine-grained boundary maps, and 2) a method of using multiplicative products of the activation maps from the final module of the CNN, and permutations of mathematical operations or activation layers thereof, to create fine-grained highly discriminative class localization of skin lesions in the form of attention maps.

In one or more implementations, the BAM is integrated into a machine-learning-based spatial measurement system to result in a BAM-Spatial Measurement component. This component uses 2D and 3D fiducial markers that allow for the measurement of the lesion area and relative depth/height as identified by the BAM system.

According to another aspect, the various components of the system are used in an augmented-reality (AR) mobile application. In one implementation, the mobile application includes the BAM saliency system and the BAM-Spatial Measurement component and the mobile application is useful in guiding skin treatments. Such skin treatments include, but are not exclusively defined by, skin lesion surgeries and topical and sub-topical treatments.

The BAM-Spatial Measurement component uses a novel reference object, 2D and 3D fiducial markers, to size the abnormality as well to standardize the images.

In one or more implementations, the CNN-BAM saliency system of the present disclosure is implemented using a mobile device or a mobile data processing system, such as a smart phone or tablet. In other implementations, the CNN-BAM saliency system is implemented as being remote from the mobile data processing system.

In one or more implementations, the CNN-saliency system of the present disclosure may be used to guide procedures, such as screening for skin abnormalities. Such skin abnormalities include lesions and other afflictions that are caused by factors internal to a patient's body. Similarly, the CNN-saliency system may be used to assist in medical interventions such as skin surgery. The CNN-saliency system may be embodied in the mobile application detailed below.

According to another aspect, there is provided a method for analyzing animal skin images using the novel CNN. In one or more implementations, the method further includes the steps of generating a skin saliency feature map produced by the described BAM system.

Referring to FIG. 1, a block diagram and flow diagram of one aspect of the present invention is illustrated. As can be seen, the system 10 includes a data processor 20 that receives an initial digital image 30. The initial image 30 shows a skin abnormality and the image 30 is sent to a processing unit 40 for classification by way of a data path 35. The processing unit 40, which includes a CNN 45, classifies the abnormality in the image 30 and produces an adjusted image 50 that is a version of the initial image 30.

The adjusted image 50 is sent back to the processor 20 and is used by an augmented reality (AR) module 60. The AR module 60 overlays the adjusted image 50 over a working image 70 of the same skin abnormality. The resulting AR feature can then be used by medical personnel in the treatment/mitigation of the skin abnormality.

In one implementation, the system 10 can be embodied in a portable data processing device with imaging capabilities. Such a data processing device may be a smart phone or a tablet. For this implementation, the processing unit 40 with the CNN is internal to the device and the data path 35 is an internal data path. Conversely, in other implementations, the processing unit 40, with the CNN, may be external and remote to the portable data processing device. For such implementations, the portable data processing device may take the initial image, transmit the initial image of the skin abnormality to the processing unit 40 by way of well-known data paths (e.g., wireless transmission, suitable networking data paths, Internet data paths, data paths leading to an on-line cloud storage/container etc., etc.). The processing unit 40, once the adjusted image has been produced, can then send the adjusted image back to the portable data processing device for use with the AR module 60. A user can thus view the adjusted image on the screen of the portable data processing device as an AR overlay atop a real time or near real time image of the skin abnormality.

Figure 2:
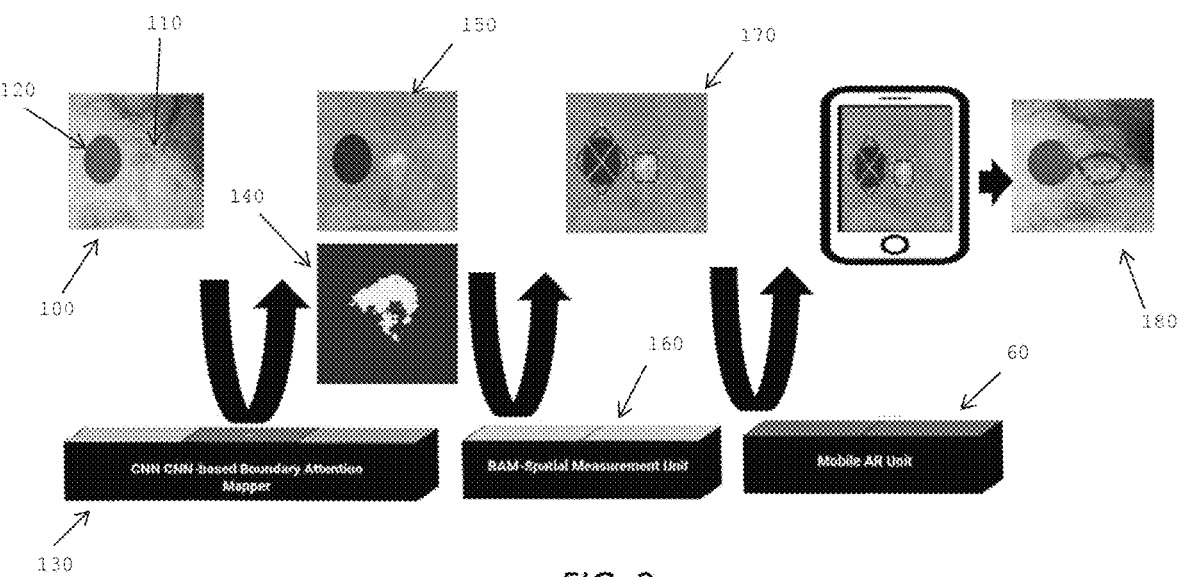
FIG. 2 is a block diagram illustrating the various components of the present invention and how these components interact with one another.

Referring to FIG. 2, the figure depicts the process flow using one implementation of the present invention. An image 100, with a lesion 110 and a 2-dimensional fiducial marker 120, is captured and used as an input for the CNN-based BAM system 130. The BAM system generates the composite boundary-attention map 140 and individual boundary map 150. These outputs are then used as input for the BAM-Spatial Measurement component 160 for measuring the identified contours of the lesion 110 using the fiducial marker 120. The resulting adjusted image 170 is a grid-marked image. The adjusted image 170 can then be used by the AR module 60 to as an overlay over a working image 180 displayed on a mobile devices screen. The overlay can then be aligned with the real-world lesion on the working image 180 and the overlay may be used to guide the clinical segmentation of the lesion area on the skin for further interventions.

Skin-Specific CNN Component

The architecture and functional components of the CNN according to one aspect of the invention are detailed with reference to FIGS. 3A-3F.

Figures 3A, 3B:
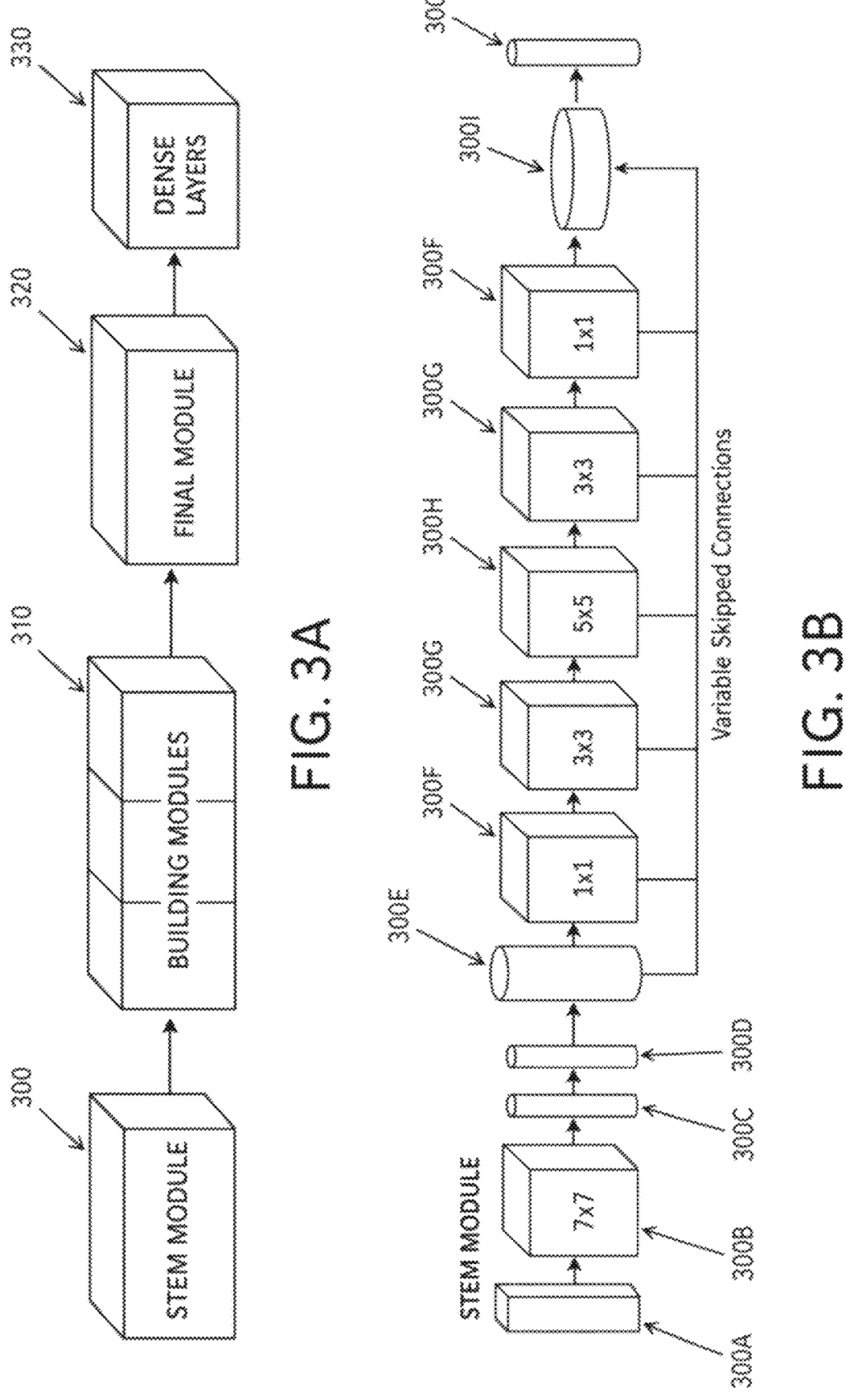
FIG. 3A-3E are block diagrams illustrating the architecture of the convolutional neural network as used in one aspect of the present invention.

Referring to FIG. 3A, illustrated are the 4 distinct blocks of neuronal layer modules of the base CNN model 10 according to one aspect of the present invention. These modules are the Stem module 300, the Building module 310, the Final module 320, and the Dense layer module 330.

Referring to FIG. 3B, illustrated is an architecture for the Stem Module 300 according to one aspect of the present invention. In this architecture, the Stem module 300 is comprised of a 224×224×3 input layer 300A, a 7×7 kernel initial convolutional layer 300B, batch normalization 300C, activation function (ReLU or Sigmoid) 300D, max pool layer 300E, followed by 5 convolutional layers 300F-300H. The convolutional blocks 300F-300H are arranged in a "fan out-fan in" sequence of kernels ranging from a 1×1 layer 300F, followed by a 3×3 layer 300G, then a 5×5 layer 300H, then again followed by a 3×3 layer 300G and then a repeat of a 1×1 layer 300F. The sequence is then followed by a concatenation operator 300I. These 5 convolutional layers have skipped connections between them and the concatenating operator 300I, in a cascade, with variability in convolutional block connections. The concatenating operator is then followed by an activation function 300D. Neuron numbers (width) of the Stem Module is guided by the embodiment of Equation 1 below as ascertained by automated hyperparameter optimization using Keras-Random Search. This Stem module 300 serves as an intrinsic component of the downstream creation of the boundary/contour mapper of the BAM component of this invention.

Figures 3C, 3D:
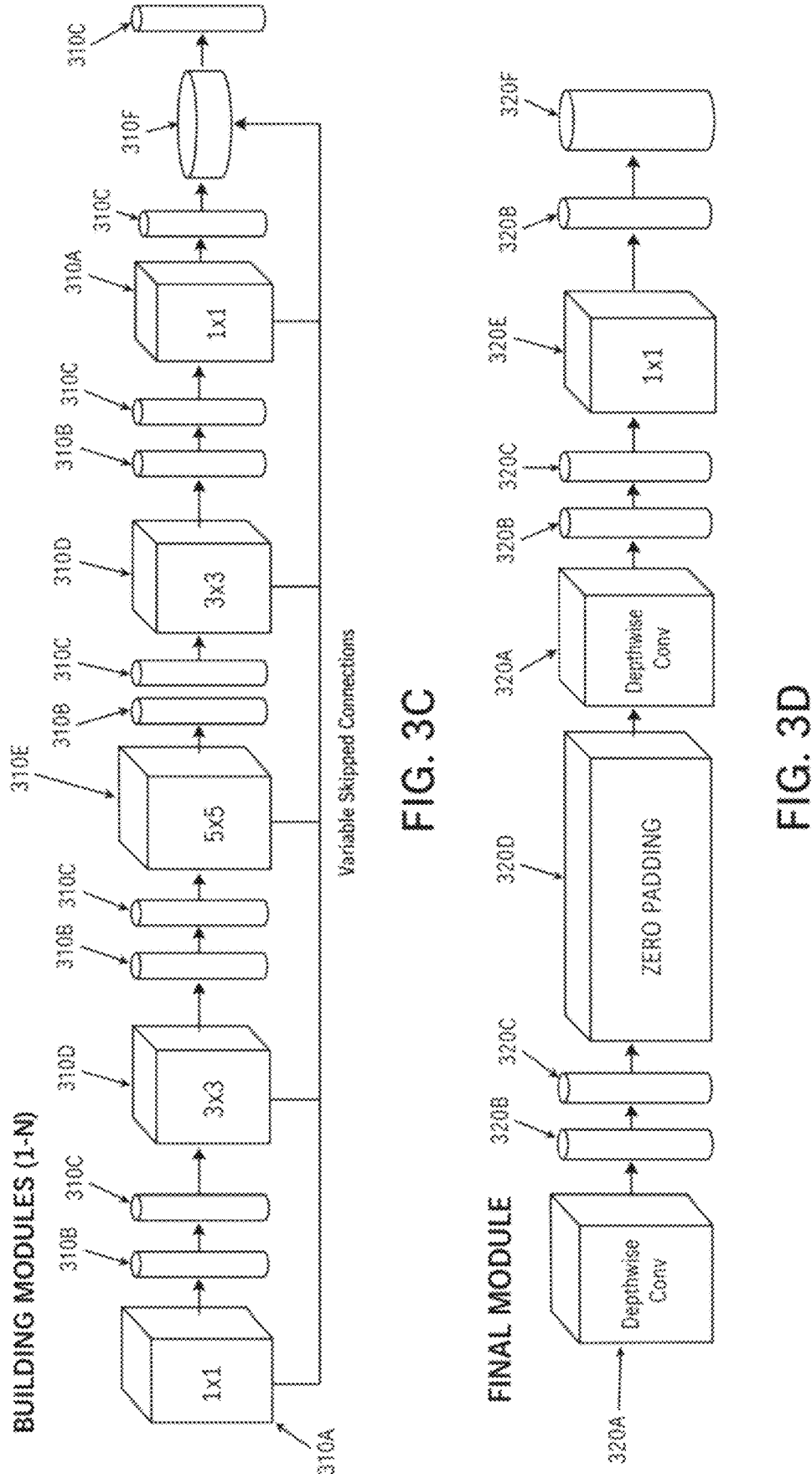

Referring to FIG. 3C, the architecture for one implementation of the Building Module 310 is illustrated. For this architecture, the Building module 310 has a variable length from one to n sub-modules. For this implementation, there are 5 convolutional blocks, with the kernels being in a fan-out-fan-in arrangement. There are variable, cascade skipped connections with interspersed batch normalization and activation function layers in between the convolutional blocks. In this implementation, there is a 1×1 layer 310A, followed by a batch normalization block 310B and then an activation function 310C. This is then followed by a 3×3 layer 310D. This 3×3 layer is then followed by another batch normalization block 310B and an activation function 310C. A 5×5 layer 310E then follows along with another batch normalization block 310B and activation function 310C. Another 3×3 layer 310D and batch normalization block 310B and activation function 310C follow. Finally, a 1×1 layer and an activation function 310C follows before a concatenating operator 310F and another activation function 310C ends the module 310. As can be seen from FIG. 3A, the Building Modules 310 are directly connected to the Stem Module 300 (front) and to the Final Module 320 (back). Neuron numbers (width) of the Building Module 310 is guided by the embodiment of Equation 1 below as ascertained by an automated hyperparameter optimization using Keras-Random Search.

Referring to FIG. 3D, the architecture for Final Module 320 is illustrated. As can be seen, the architecture comprises a sequential connection of a depth-wise convolutional block 320A, batch normalization 320B, activation layer 320C, and zero padding layer 320D. This is then followed by another depth-wise convolutional block 320A, batch normalization 320B, and activation layer 320C. After this is a 1×1 kernel convolutional layer 320E, batch normalization 320B and a final max pool layer 320F. Neuron numbers (width) of the Final Module 320 is guided by the embodiment of Equation 1 as directed by an automated hyperparameter optimization using a Keras-Random search. This module 320 serves as an intrinsic component of the downstream creation of the attention/saliency mapper of the BAM component of one aspect of the present invention.

Figure 3E:
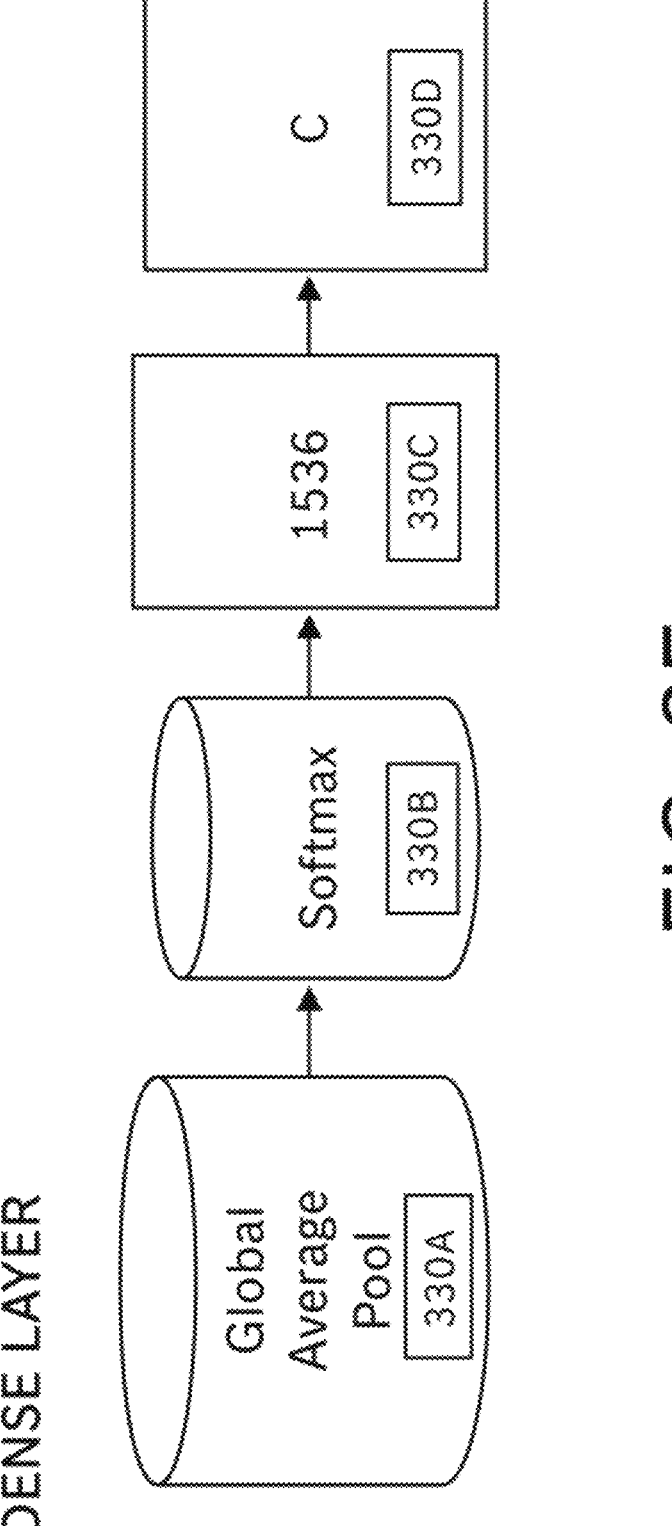

Referring to FIG. 3E, illustrated is the architecture for Dense Layer 330. As can be seen, the Dense Layer module 330 is comprised of a global average pool layer 330A, a softmax activation layer 330B, and two or more fully-connected dense layers (multi-layered perceptron). The first layer 330C is initially created using 1536 neurons, and the number of the last layer 330D is guided by the value C, the number of required classes or permutations thereof, which is related to the Building Modules (M) as in Equation 1. The above Dense layer module architecture is also optimized using Keras-Random Search.

For greater clarity, the Stem block or module of the CNN is the first block of the CNN and is primarily made up of 2D convolutional layers. Unlike other CNNs, this Stem block has variable skipped connections (n=1 to 6). The stem block according to the present invention provides the contour/boundary maps that the BAM extracts to visualize the boundary of a skin abnormality such as a lesion.

The Building module of the CNN is the variable basic block that can be stacked (1–N), to increase the depth of the CNN, and also uses variable skipped connections. The building module is the primary computational block of the open, directional graph system of the CNN.

The Final module detailed above captures and downscales all information from the previous blocks before feeding these into the decision/dense layer. This Final module includes depth-wise convolutions blocks. This Final module is used by the BAM component to capture attention pixels of the system.

The Dense layer detailed above, primarily a multilayer perceptron, is variable in terms of depth and width of neuronal layers. This Dense layer functions by changing the dimensions of the vectors from previous layer. The Dense layer is a fully connected layer with no convolutional layers and is optimized for skin lesions. This Dense layer provides the final outputs of the CNN.

2) Scaling & Optimization i) Architecture Scaling

The Building Modules 310 is a variable module, where the number of sub-blocks (each consisting primarily of 5 convolutional layers 120 interspersed with batch normalization 130 and activation layers 140) can be increased as per the needs of a changing image dataset size used for training and/number of classes (C) of the classification task:

$$M = a\sqrt{\frac{1+\sqrt{5}}{2}} \times \frac{c}{2} \text{ and } n > 8 \times M \qquad \text{(Eqn. 1)}$$

where M=number of building modules (rounded to next integer), C=number of classes (equivalent to dense layers), n=number of neurons in a layer, and a is a user-specific value to compensate for dataset size.

It should be noted that the final scaling is also dependent on hyperparameter optimization as described above.

The Building Module (M) architecture scaling schema is derived from the golden ratio value, which has been used in neural networks for determining parameters unrelated to this invention [16]. The scaling of M, due to a change in the number of classes, is determined by Equation 1 above or as directed by the hyperparameter optimization. Furthermore, the scaling of M, due to dataset size change, is guided by a user-specific value, given by variable a in Equation 1, or the value with the best training parameters as indicated by the results of hyperparameter search using a Keras-Random search. Additionally, the minimum number of neurons in a layer is provided as 8×M and this also applies to the non-Building Modules.

ii) Activation Function Approximation

Taylor series operations allow for an accurate approximation of the underlying function in a dataset by performing calculations to the nth degree [17]. In some implementations, the present invention uses the square root of the golden ratio value to calculate the appropriate nth value to be used in conjunction with either a Sigmoid or a ReLU activation layer:

$$n = a\sqrt{\frac{1+\sqrt{5}}{2} \times \frac{M}{2}} \qquad \text{(Eqn. 2)}$$

where n denotes the Taylor Series approximation to nth degree, M is number of building modules, and a is a user-specific value to compensate for dataset size.

iii) ReLU Layer Weight Initialization

In some implementations, the present invention uses a unique weight initialization operation, for ReLU layers, which is the product of the number of neurons incoming to the activation layer (N), and the square root of the golden ratio value, or mathematical permutations thereof:

$$v^2 = a\sqrt{\frac{1+\sqrt{5}}{2}} N \qquad \text{(Eqn. 3)}$$

where v is the weight initialization factor for a ReLU activation function, N is the number of neurons of the incoming layer, and a is a user-specific value to compensate for dataset size.

The golden ratio multiplier makes the weight initialization non-arbitrary, like the He/Kaiming or Xavier method of weight initialization. However, unlike these traditional weight initialization methods, this invention component is scalable by a user-specified factor, a, dependent on the size of the dataset and by indications of the hyper-parameter tuning.

iv) Texture Optimization

In one or more implementations, the present invention uses an image pre-processing step, a derivation of the classical grey-level co-occurrence matrix (GLCM) operation (mathematical permutation of Equation 4), as a method for refining and distinguishing texture features of "abnormal" skin, which includes but is not exclusive to skin lesions from normal skin:

$$sGLCM = P[a'1, a''2] \qquad \text{(Eqn. 4)}$$

where P is the joint probability, a1 is the reference pixel and a2 is another pixel d vector apart from a1. For skin-specificity, a'1 is a pixel in the "area-of-abnormality" on the skin (Ex: lesion) and a''2 is a pixel from the normal skin.

The skin-specific co-occurrence matrix calculates the joint probabilities of a pair of pixels from the image like the traditional GLCM [20]. However, the operator does so by taking a reference pixel (a'1) from the abnormal skin area and matches it to a second set of pixels (a''2) in the normal skin area, which are a vector d away from the reference pixel. Here, the base matrix M is a 16×16 matrix, and the measure of choice is a derivation of the Entropy (mathematical permutation of Equation 5), which is a log product of the joint probabilities (P) of the two class of pixel entities:

$$E = \sum_{a'1}^{M-1} \sum_{a''2}^{M-1} P[a'1, a''2] \log_2 P[a'1, a''2] \qquad \text{(Eqn. 5)}$$

where M=16×16 matrix, and P[a'1, a''2] are the joint probabilities of two pixels on the image, with the reference pixel in the skin abnormality.

Training Dataset

1) Specialized Dataset

Most CNNs used for skin-specific classification tasks have used large pre-trained models, with millions of parameters, that were trained on open-source ImageNet dataset [6,18]. These were subsequently trained on small skin datasets, such as the dermatoscopic open datasets from the ISIC [2]. As the large datasets like ImageNet are of generic objects and the smaller datasets like ISIC are of highly detailed dermatoscopic skin lesions, they are not representative of abnormal/normal skin images taken from mobile devices.

Moreover, the open-source skin datasets are restricted to a few skin abnormalities classes. Specialized dataset databases (such as that available from Skinopathy™) contain clinically curated datasets of high-quality skin abnormality mobile-device and dermatoscopic images. Datasets such as these preferably include over many skin abnormalities, including single cancerous lesions, dermatological diseases such as acne, burns, and pathological wounds, collected over several years. Using such specialized databases, or subsets thereof, in conjunction with the training schema for high-level feature extraction from larger generic image datasets or skin-specific open datasets, advances the specificity of the present invention for images of the skin.

2) Training Schema

Figure 4:
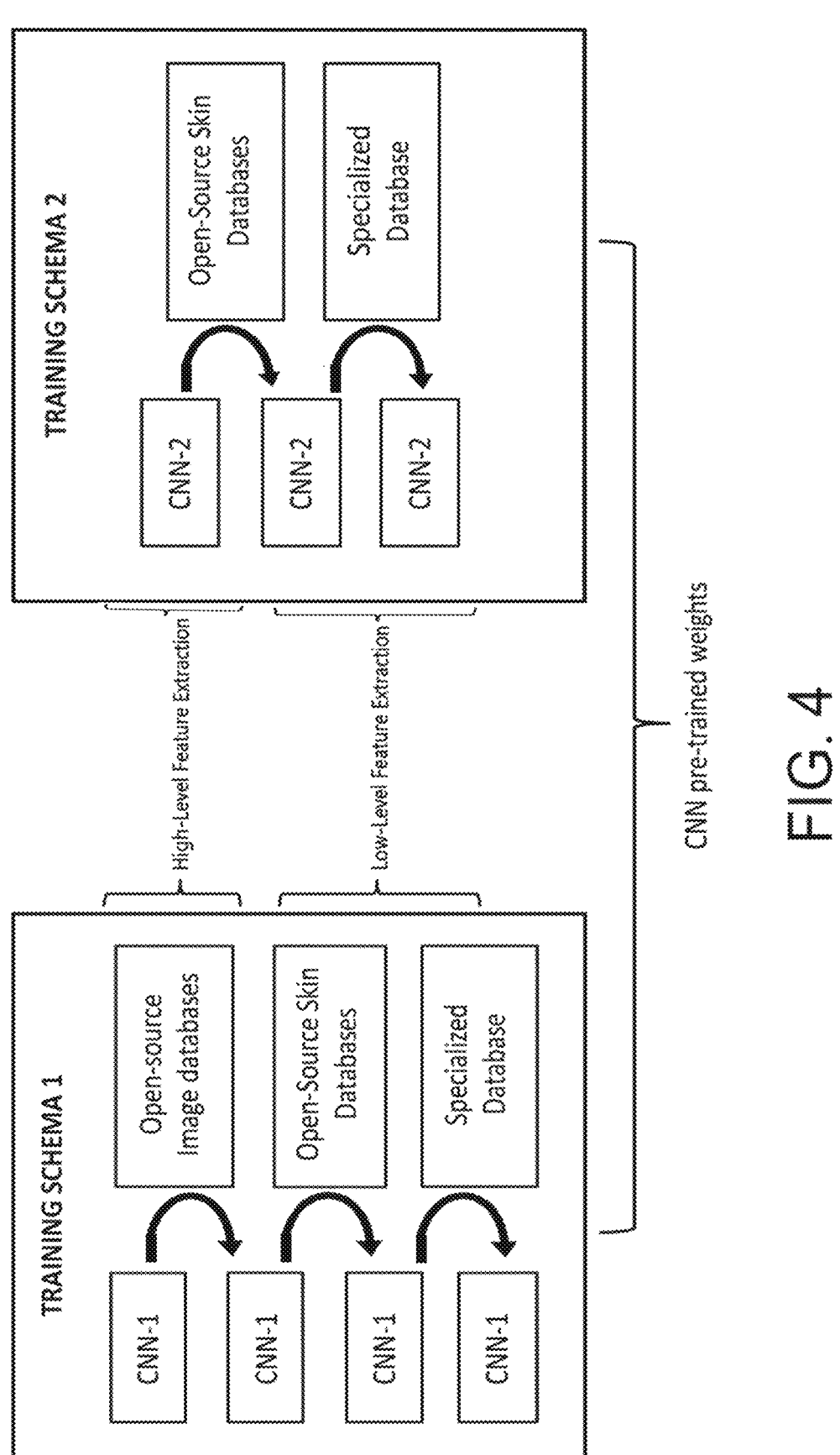
FIG. 4 is a flow diagram illustrating one training schema which may be used to train the CNN detailed below.

Open-source image datasets such as ImageNet, comprising of over 1.4 million images of 1000 objects, allows CNN models to train and/extract high-level image features such as edges and curvatures [6,8]. Skin-specific datasets, such as the ISIC curation of skin diseases [2], allows for CNN models to be trained on skin-specific features, but is limited by being dermatoscopic and only for a few skin diseases. In some implementations, the CNN of the present disclosure uses two training strategies to extract and train on high level and skin-specific features, including lesions. The strategy avoids training on any proprietary/closed source database, apart from the specialized image database from companies such as Skinopathy™. The training strategy, schematically illustrated in FIG. 4, uses a cascade process of training the CNN to learn high-level general features on larger open-source image datasets of random objects and skin specific images, before training on specialized image databases. In addition, for low-level, fine-grained features, the CNN is trained only on open-source skin specific images and on the skin images 550 from specialized databases. The final iteration of the model uses pretrained weights, or permutations thereof, for these two learning strategies.

Saliency Map Generator/Boundary Attention Mapper Component

Figure 5:
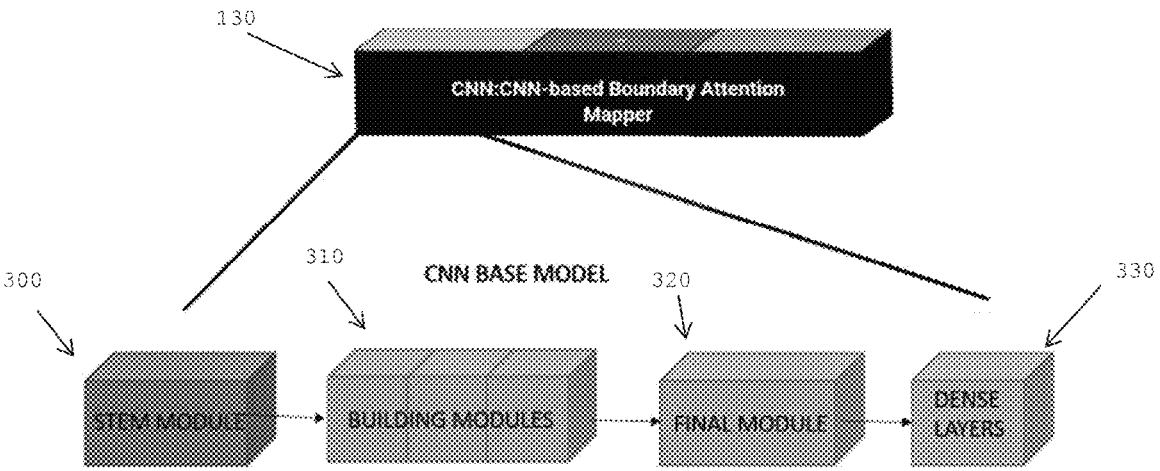
FIG. 5 details the components of the CNN as used in the BAM according to one aspect of the present invention.

FIG. 5 shows the CNN-BAM module 130 with 4 distinct blocks of neuronal layer modules of the base CNN model as detailed above: Stem Module 300, Building Module 310, Final Module 320, and Dense Layer 330.

Figure 6:
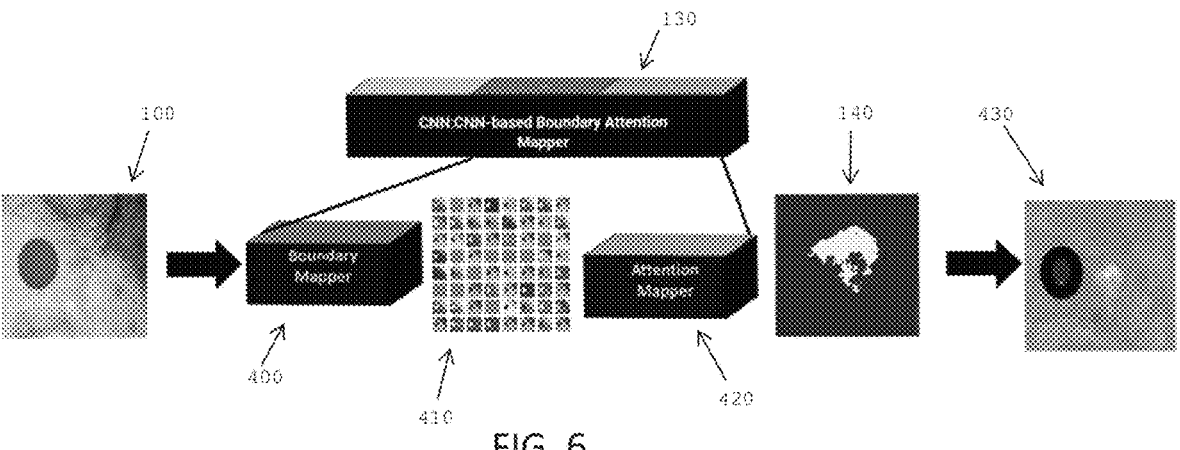
FIG. 6 illustrates an overview of the process and the components used in progressing from an initial image of a skin abnormality to the creation of an adjusted image which may be used as an overlay by an AR module.

FIG. 6 depicts the process flow of images into the other portions of the BAM module 130. Once the image has been classified, the other subcomponents of the BAM module (e.g. the saliency generator) can be used to compute the boundary-attention map. As can be seen from FIG. 6, the subcomponents use a range of operations to compute a visualization of the image that can be used for salient object detection for further processing. Given the input image and class of interest, the saliency/BAM module goes through the following steps:

i) The input initial image 100 (may be an RGB color image) is resized and forward propagated into the CNN layers.

ii) The Boundary Mapper 400 extracts feature maps 410 from the stem module 300 of the CNN. The channel index from the feature maps 410 with high resolution and boundary accuracy is selected as pre-determined by the user or by way of an iterative function. All tensor information continues to be passed through image classification computations of the CNN to obtain a raw score for the class by the final module 320 feature map activations. This is passed to the dense layer module 330, which is a specialized layer for the skin dataset, for final class prediction.

iii) The Attention Mapper 420 utilizes the class activation map, with gradients, from the top activation layer of the CNN, with or without other layer maps from the final module 320, as the base input. The Attention mapper 420 uses pixel threshold (0.5 or permutations thereof), to remove the non-decision pixels in the generic gradient-based, class activation map. This threshed map is correlated with selected channel(s) and feature map(s) 410 from the Boundary mapper 400 (created from the stem module 300 of the CNN) in an iterative manner. The composite Attention Maps 140 that highly correlate to the Boundary Maps (i.e. having a mean difference <0.05 or a lower user-selected mean difference) is used to create the final BAM map 430.

In one or more implementations of this invention, the final composite attention Map 140 is given by a permutation of [Equation 5]:

$$\left\{ \sum [\text{Boundary Map}] \cdot \sum [\text{Attention Map}] - \chi \cdot [f : \chi \rightarrow \chi] \right\} \quad \text{(Eqn. 5)}$$

where $\chi$ represents the pixel threshold for correlating the attention and boundary maps, and $f:\chi \rightarrow \chi$ represents the iteration of this threshold until mean difference between maps are <0.05.

BAM-Spatial Measurement Component

Figure 7:
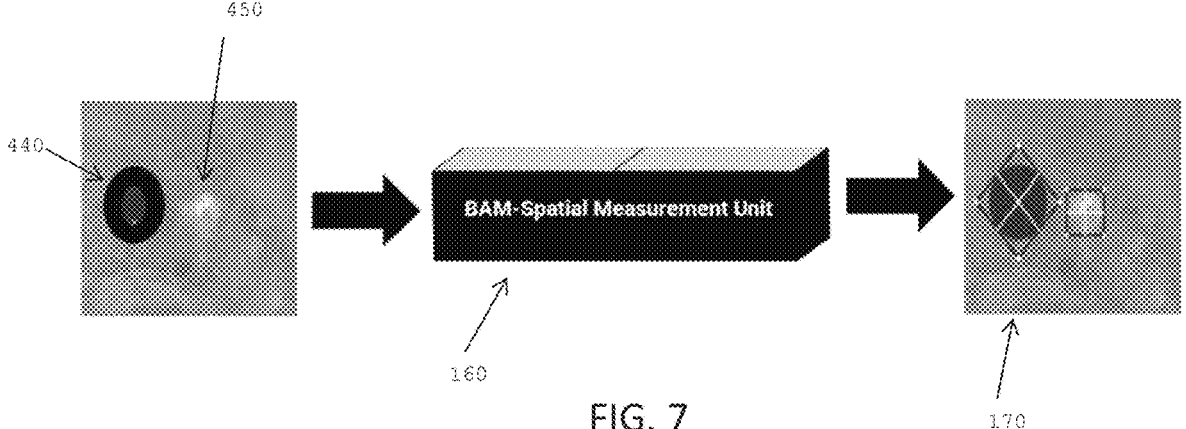
FIG. 7 illustrates the use of a BAM-Spatial measurement component in the creation of an adjusted image.

FIG. 7 shows the output tensor from BAM module 130 as the input to a spatial measurement component 160. The spatial measurement component 160 uses the fiducial marker image 440, which has a known color and diameter in the attention map 150, to calculate the 2D (length×width and area) measurements of the contour mask pixels of the lesion/skin abnormality 450. This information is produced by the contour/boundary mapper unit of the BAM module 130. The measurement unit places a digitally-generated grid box on the reference marker and identified lesion area with the measured values as labels on the adjusted image 170.

Mobile Augmented Reality (AR) Unit

Figure 8:
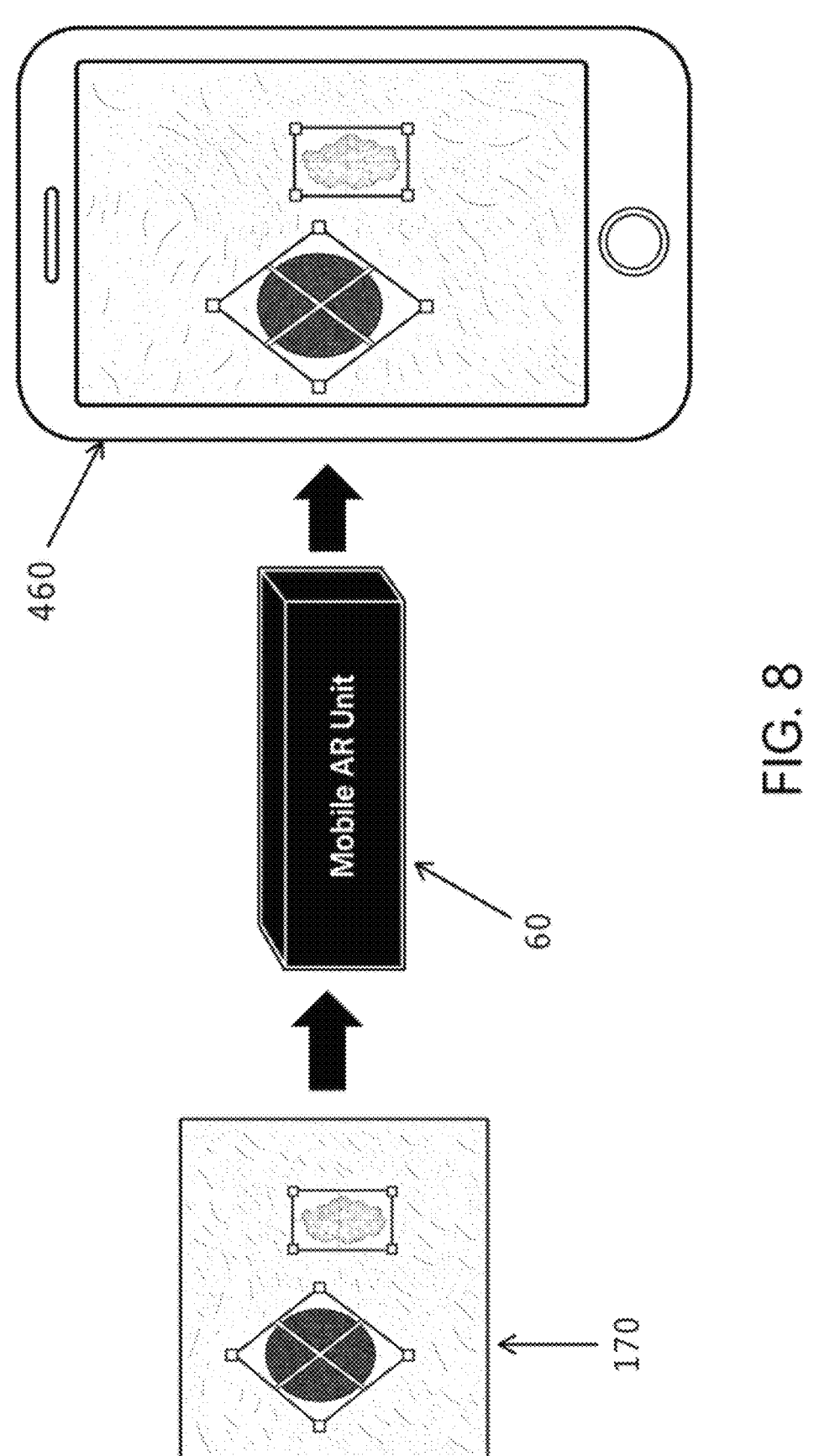
FIG. 8 shows the data flow that uses a mobile AR unit according to one aspect of the present invention.

FIG. 8 depicts the adjusted image 170 (the output of the BAM-Spatial Measurement component 160) being used as the input into the augmented reality component 60. The AR component 60 converts this adjusted image and uses it as an overlay on a screen of a mobile device 460.

Fiducial Markers

Figure 9:
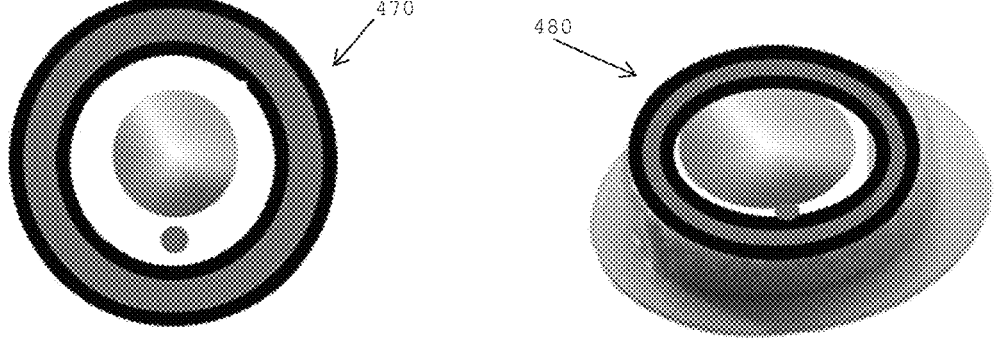
FIG. 9 illustrates a 2D and a 3D fiducial marker for use with various aspects of the present invention.

FIG. 9 shows one version of 2D and 3D fiducial marker designs, as replacements to the generic, blue-colored fiducial marker shown in FIG. 2. The 2D Marker 470 is an adhesive circular sticker that is less than 1 inch in diameter. It has an illustrated colour wheel design (or a design with a subset of colors) to optimize size detection, color calibration of the lesion colors, and color calibration of the image-capture mobile device. The 3D Marker 480 is an adhesive, circular, synthetic, skin-compatible tag that is approximately less than 1 inch in diameter. In one implementation, it has a height of less than 0.2 inch, with an illustrated 2D design on the non-adhesive surface.

Based on the above descriptions, it should be clear that, in one aspect, the various components, including the CNN, BAM and spatial measurement components described above, are used in conjunction with an augmented reality mobile-device application. The application can then be used to guide skin treatments (including lesion surgeries).

For better clarity, the system and flow shown in FIG. 2 depicts one specific aspect of the present invention: a mobile-device application using the above-described CNN, BAM, BAM-based measurement components previously as the back end of the application. These components are used to detect a skin abnormality, to classify that abnormality using the CNN, and to generate contour and attention maps. A BAM-Spatial Measurement component measures the size of the skin abnormality using a fiducial marker in the image as a reference point and generates gridlines over the lesion contour map to result in an adjusted image. The adjusted image is then used by the AR unit as an overlay on the screen of the device as a real-time or near-real time image of the skin abnormality is displayed. Specifications of the contour size and shape may be user-guided to allow for contextual flexibility and to meet medical requirements. As should be clear, the adjusted image, with the contour map and grid scale, will be displayed on the mobile device as an augmented-reality object overlaid with the real-world view of the skin abnormality in the background. A clinician can then make contour marks of around the skin abnormality using the augmented reality object.

Figure 10:
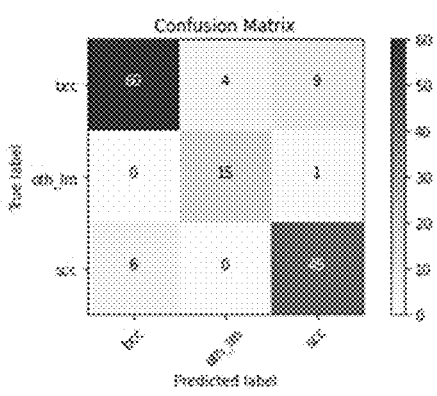
FIG. 10 details the performance results of one version of the CNN according to another aspect of the present invention.

To illustrate the efficacy of the specifically configured CNN of the present invention, performance data for one version of this CNN is detailed in FIG. 10. FIG. 10 shows the performance metrics of one version of CNN detailed above. As noted above, this CNN is trained on smartphone camera-images for 3 types of lesion classes. The classes were basal cell carcinoma (BCC), another group of lesions (Other LM), and squamous cell carcinomas (SCC). The performance metrics indicates an 86% average F1 accuracy. The confusion matrix indicates low false positive and false negative values for the 3 classes.

Figure 11:
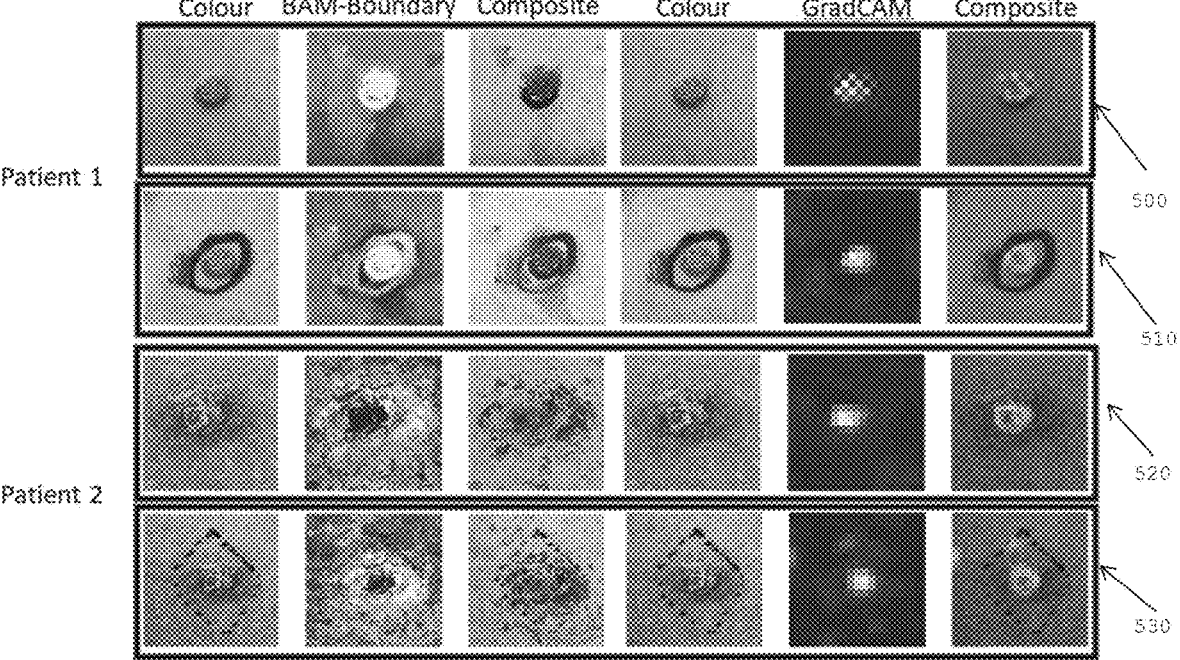
FIG. 11 illustrates the results of the BAM system in images from two carcinoma patients.

Referring to FIG. 11, there is depicted the results of the BAM system (boundary subunit only) on images from two squamous cell carcinoma (SCC) patients. The top horizontal panel 500's first three images depict colour, BAM-Boundary map, and a composite image, respectively, from Patient 1. This is placed in juxtaposition to the last three images (colour, GradCAM and composite, respectively) for a comparison of this Boundary Component of the BAM system of this invention, with the state-of-the-art GradCAM saliency system. Panel 510 depicts the same SCC lesion but includes a surgeon's excision margins. Panel 520 and 530 depict the same results as described above for panel 500 and panel 510 but for Patient 2.

Figure 12:
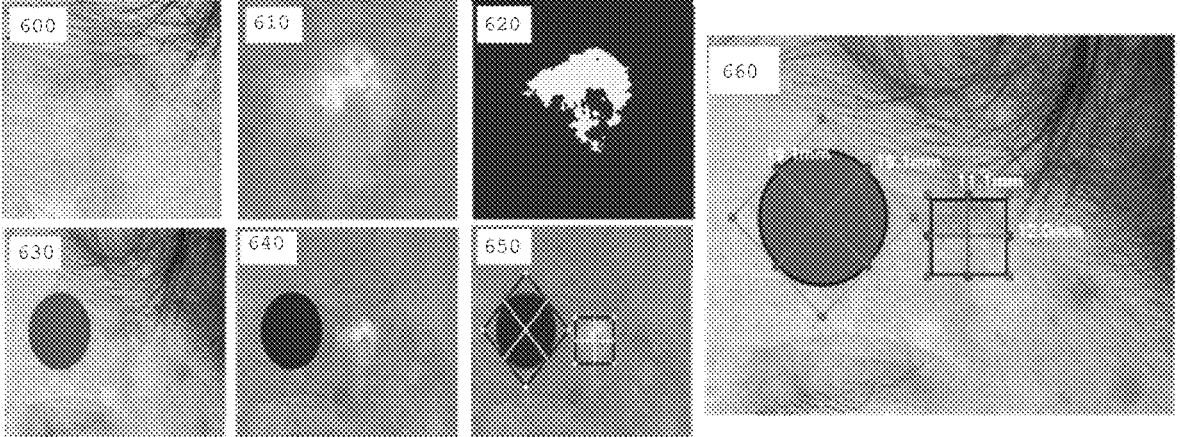
FIG. 12 shows the results for both the BAM and the BAM-spatial measurement component and how the size of the skin abnormality (a basal cell carcinoma) is measured.

Referring to FIG. 12, shown are the results of both the BAM system (Boundary and Attention subunits) and the BAM-Spatial Measurement component as described above. An image of a basal cell carcinoma lesion 600 acts as input for the CNN-BAM system, as described above. The boundary map is created 610, which is used with the output of the Attention subunit of this invention, to create a composite BAM map 620. For the BAM-Spatial Measurement unit, an image 630 of the lesion with a fiducial marker (here a blue 19 mm diameter sticker label is used and applied next to the skin abnormality), is used as input. The BAM unit creates a boundary map 640, which is then used to measure the fiducial marker and the boundary map of the lesion 650. An alternative output of the spatial measurement subunit, without the BAM map overlay, is shown in 660.

Figure 13:
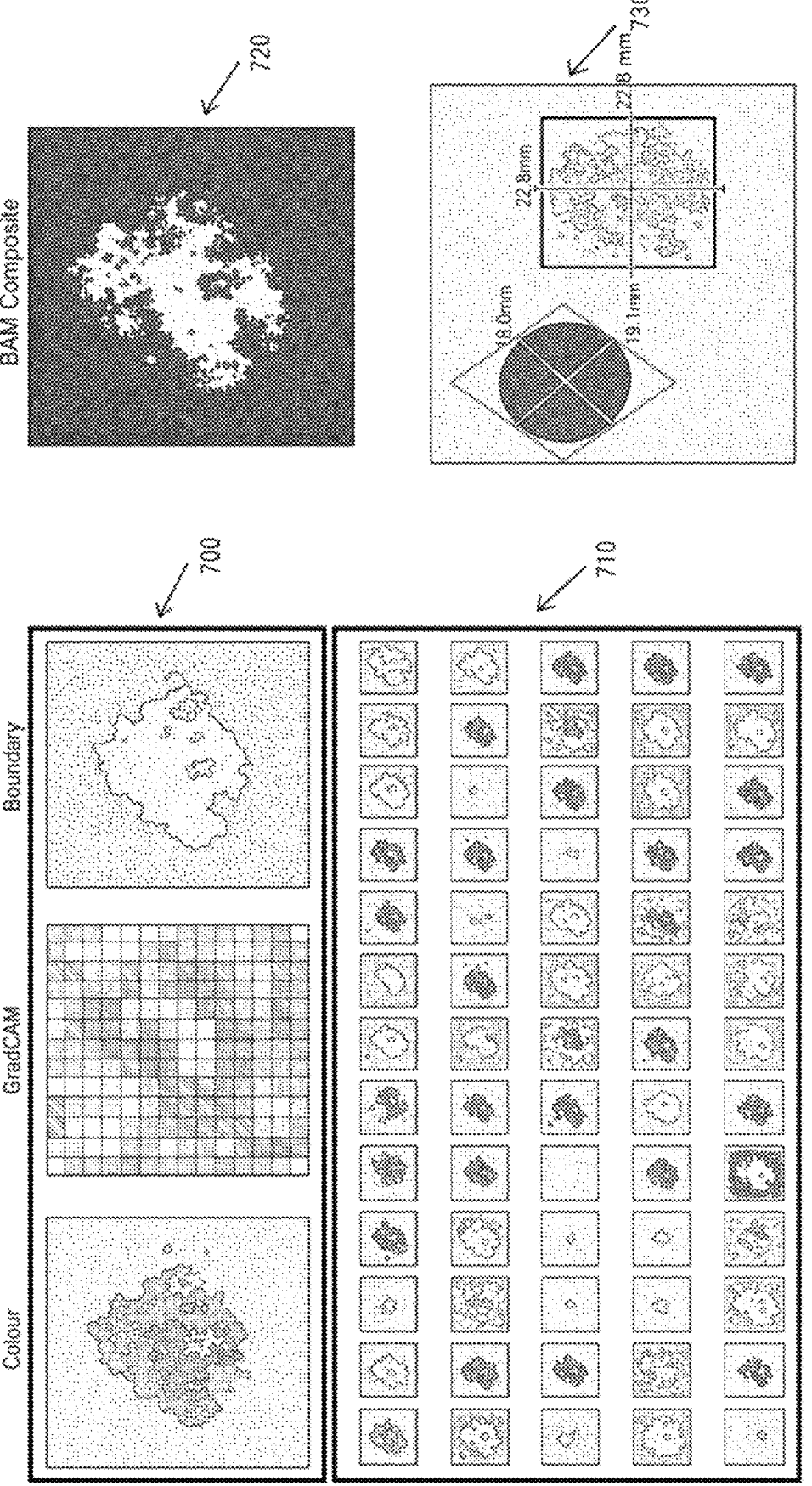
FIG. 13 shows the results for the BAM and BAM-spatial measurement and how the boundaries and size of the skin abnormality are determined for a melanoma patient.

Referring to FIG. 13, shown are the results of the BAM and BAM-Spatial Measurement units described above using a lesion image from a melanoma patient (Panel 700, left colour image). Panel 700 compares the input colour image, the highly-abstract GradCAM saliency map (middle image, panel 700), and the high-resolution contours in the BAM-boundary map (right image, panel 700) results produced according to another aspect of the present invention. The intermediate activation maps from the CNN (see panel 710), which the BAM component uses to identify the optimal lesion boundary, is also depicted here. Image 720 depicts the composite final BAM image (an integration of the optimal BAM produced boundary and the optimal attention map) produced by the BAM system according to another aspect of the present invention. The image 720 uses the selected boundary map(s), from panel 710, and the modified attention map created by using a function of the class activation map, as described in the Saliency Map/Boundary Attention Mapper section above. Image 730 depicts the resulting spatial measurement of the melanoma lesion, with all pixels of the BAM maps included, using a generic fiducial marker as shown in FIG. 2.

As noted above, for a better understanding of the present invention, the following references may be consulted. Each of these references is hereby incorporated in their entirety by reference.

1. The Global Burden of Skin Disease in 2010: An Analysis of the Prevalence and Impact of Skin Conditions. Hay, R. J. et al. *Journal of Investigative Dermatology* 134, 1527-1534 (2014).
2. Artificial intelligence-based image classification methods for diagnosis of skin cancer: Challenges and opportunities" Goyal, M., Knackstedt, T., Yan, S., Hassanpour, S. *Computers in Biology and Medicine*, Volume 127, 2020,
3. A comparison of deep learning performance against health-care professionals in detecting diseases from medical imaging: a systematic review and meta-analysis Liu, X., Faes, L., Kale, A. U., et al. 2019, *The Lancet Digital Health*, Volume 1, Issue 6, e271-e297
4. Dermatologist-level classification of skin cancer with deep neural networks. Esteva, A., Kuprel, B., Novoa, R. et al. *Nature* 542, 115-118 (2017).
5. A deep learning system for differential diagnosis of skin diseases. Liu, Y., Jain, A., Eng, C. et al 2019. *Nature Medicine* volume 26, pages 900-908(2020)
6. ImageNet classification with deep convolutional neural networks" Krizhevsky, A. Sutskever, I., and Geoffrey E. Hinton. 2017. *Commun. ACM* 60, 6, 84-90. (2017)
7. A survey of the recent architectures of deep convolutional neural networks. Shan, A., Sohail, A., Zahoora, U. et al. et al. *Artif Intell Rev* 53, 5455-5516 (2020).
8. "Supervised Saliency Map Driven Segmentation of Lesions in Dermoscopic Images" Jahanifar, M., Zamani Tajeddin, N., Mohammadzadeh Asl B. and Gooya, A., in *IEEE Journal of Biomedical and Health Informatics*, vol. 23, no. 2, pp. 509-518, (2019)
9. "Learning important features through propagating activation differences", Avanti Shrikumar, Greenside Peyton and Anshul Kundaje; arXiv preprint arXiv: 1704.02685 (2017).
10. "Contextual explanation networks", Maruan Al-Shedivat, Avinava Dubey, Eric P. Xing; arXiv preprint arXiv: 1705.10301 (2017).
11. "Striving for Simplicity: The All Convolutional Net", J. T. Springenberg, A. Dosovitskiy, T. Brox, and M. A. Riedmiller; CoRR, abs/1412.6806 (2014).
12. "Deep inside convolutional networks: Visualising image classification models and saliency maps", Karen Simonyan, Andrea Vedaldi and Andrew Zisserman; arXiv preprint arXiv: 1312.6034 (2017).
13. "Grad-CAM: Visual Explanations from Deep Networks via Gradient-Based Localization", Ramprasaath R. Selvaraju, Michael Cogswell, Abhishek Das, Ramakrishna Vedantam, Devi Parikh, Dhruv Batra; In ICCV, pp. 618-626. (2017).
14. "Smooth Grad-CAM++: An Enhanced Inference Level Visualization Technique for Deep Convolutional Neural Network Models", Daniel Omeiza, Skyler Speakman, Celia Cintas, Komminist Weldemariam *ArXiv*, abs/1908.01224 (2019).
15. "New Gradient-Weighted Adaptive Gradient Methods With Dynamic Constraints", D. Liang, F. Ma, and W. Li; in IEEE Access, vol. 8, pp. 110929-110942, (2020).
16. "The Golden Ratio of Learning and Momentum", Jaeger, S. S. arXiv preprint arXiv: 2006.04751, 2020

17. Neural Taylor Approximations: Convergence and Exploration in Rectifier Networks, Balduzzi, D., McWilliams, B. and Butler-Yeoman, T., 2018, 1611.02345, arXiv 18. Delving Deep into Rectifiers: Surpassing Human-Level Performance on ImageNet Classification. He, K., Zhang, X., Ren, S. and Sun, J., 2015, 1502.01852 arXiv 19. A Survey on Activation Functions and their relation with Xavier and He Normal Initialization, Datta, L., 2020, 2004.06632 arXiv 20. Grey level Co-Occurrence Matrices: Generalisation and Some New Features, Sebastian, V. B., Unnikrishnan, A., Balakrishnan, K. IJCSEIT, Vol. 2 ▦▦, 2012

It should be clear that the various aspects of the present invention may be implemented as software modules in an overall software system. As such, the present invention may thus take the form of computer executable instructions that, when executed, implements various software modules with predefined functions.

Additionally, it should be clear that, unless otherwise specified, any references herein to 'image' or to 'images' refer to a digital image or to digital images, comprising pixels or picture cells. Likewise, any references to an 'audio file' or to 'audio files' refer to digital audio files, unless otherwise specified. 'Video', 'video files', 'data objects', 'data files' and all other such terms should be taken to mean digital files and/or data objects, unless otherwise specified.

The embodiments of the invention may be executed by a computer processor or similar device programmed in the manner of method steps, or may be executed by an electronic system which is provided with means for executing these steps. Similarly, an electronic memory means such as computer diskettes, CD-ROMs, Random Access Memory (RAM), Read Only Memory (ROM) or similar computer software storage media known in the art, may be programmed to execute such method steps. As well, electronic signals representing these method steps may also be transmitted via a communication network.

Embodiments of the invention may be implemented in any conventional computer programming language. For example, preferred embodiments may be implemented in a procedural programming language (e.g., "C" or "Go") or an object-oriented language (e.g., "C++", "java", "PHP", "PYTHON" or "C#"). Alternative embodiments of the invention may be implemented as pre-programmed hardware elements, other related components, or as a combination of hardware and software components.

Embodiments can be implemented as a computer program product for use with a computer system. Such implementations may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or electrical communications lines) or a medium implemented with wireless techniques (e.g., microwave, infrared or other transmission techniques). The series of computer instructions embodies all or part of the functionality previously described herein. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink-wrapped software), preloaded with a computer system (e.g., on system ROM or fixed disk), or distributed from a server over a network (e.g., the Internet or World Wide Web). Of course, some embodiments of the invention may be implemented as a combination of both software (e.g., a computer program product) and hardware. Still other embodiments of the invention may be implemented as entirely hardware, or entirely software (e.g., a computer program product).

A person understanding this invention may now conceive of alternative structures and embodiments or variations of the above all of which are intended to fall within the scope of the invention as defined in the claims that follow.

We claim:

1. A system for use with digital images, the system comprising:
   a digital imaging device on a mobile computing device configured to produce an initial digital image of a basal cell carcinoma (BCC) or a squamous cell carcinoma (SCC) of a patient;
   a processor configured to receive the initial digital image and to receive at least one adjusted image;
   a data communication path configured to send the initial digital image to at least two processing units, including:
      a first processing unit comprising at least one convolutional neural network (CNN) configured to classify the initial digital image and to generate a first adjusted image by creating a composite Boundary-Attention Map (BAM) whose mean difference from a boundary map is less than 0.05; and
      a second processing unit configured to measure three-dimensional (3D) features in the initial digital image using a 3D fiducial marker and to generate a second adjusted image; and
   an overlay module configured to overlay at least one of the first adjusted image and the second adjusted image over a working image of the same carcinoma on the mobile computing device as an augmented-reality (AR) overlay.

2. The system according to claim 1, wherein the 3D fiducial marker has a diameter less than one inch and a height less than 0.2 inch.

3. The system according to claim 1, wherein the overlay module presents gridlines and measured dimensions derived from the 3D fiducial marker.

4. The system according to claim 1, wherein the first processing unit's CNN comprises a stem block with variable skipped connections, a building module, a final module, and a dense layer.

5. The system according to claim 4, wherein attention pixels in the initial digital image are captured by the final module and combined with boundary maps extracted from the stem block to create the BAM.

6. The system according to claim 1, wherein the AR overlay is displayed in real-time or near-real-time on the mobile device while a clinician marks excision margins.

7. The system according to claim 1,
   wherein the at least two processing units are remote from the mobile device.

8. A method for processing an initial digital image of a skin cancer comprising a basal cell carcinoma (BCC) or a squamous cell carcinoma (SCC), the method comprising:

by way of a data processor, receiving said initial digital image;

sending the initial digital image to a first processing unit comprising a convolutional neural network (CNN);

using the CNN to classify at least one element in the initial digital image and to generate a first adjusted image by forming a composite BAM whose mean difference from a boundary map is less than 0.05;

using a second processing unit to measure 3D features of the skin cancer in the initial digital image using a 3D fiducial marker, and to generate a second adjusted image;

by way of the data processor, receiving the first adjusted image and the second adjusted image; and overlaying at least one of the first adjusted image and the second adjusted image over a working image of the skin cancer as an AR overlay on a mobile device.

9. The method according to claim 8, further comprising capturing contour data and attention pixels from said initial digital image.

10. The method according to claim 8, further comprising determining a 3D relative size of the skin cancer using the 3D fiducial marker.

11. A non-transitory computer readable medium storing instructions that, when executed, implements a convolutional neural network (CNN) comprising:

a stem block with variable skipped connections;

a building module;

a final module; and a dense layer;

the instructions causing the CNN to:

extract boundary maps from stem-block features;

capture attention pixels from the final module; and form a composite BAM whose mean difference from a boundary map is less than 0.05 for use in generating an adjusted image of a skin abnormality.

12. The non-transitory computer readable medium according to claim 11, wherein said CNN is trained on a dataset comprising images taken using mobile devices.

13. The non-transitory computer readable medium according to claim 11, wherein the adjusted image is output for AR overlay on a mobile device during treatment planning or surgery.

\*　\*　\*　\*　\*